US005304165A

United States Patent [19]

Haber et al.

[11] Patent Number: 5,304,165

[45] Date of Patent: Apr. 19, 1994

[54] SYRINGE-FILLING MEDICATION DISPENSER

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 805,503

[22] Filed: Dec. 9, 1991

[51] Int. Cl.⁵ .......................... A61M 1/00

[52] U.S. Cl. .......................... 604/411

[58] Field of Search .......................... 604/232, 82, 86, 87, 604/411–415; 141/25–27, 105, 107, 329, 375, 46

[56] References Cited

U.S. PATENT DOCUMENTS

| | | | |
|---|---|---|---|
| 3,853,158 | 12/1974 | Whitty | 141/375 |
| 3,932,136 | 1/1976 | Stichney | 141/105 |
| 4,296,785 | 10/1981 | Vitello et al. | 141/105 |
| 4,434,820 | 3/1984 | Glass | 141/375 |
| 4,505,709 | 3/1985 | Froning et al. | 604/411 |
| 4,856,567 | 8/1989 | Cosmai | 604/411 |
| 4,877,065 | 10/1989 | Lamboy et al. | 141/329 |
| 4,998,570 | 3/1991 | Strong | 141/27 |

*Primary Examiner*—C. Fred Rosenbaum
*Assistant Examiner*—Manuel Mendez
*Attorney, Agent, or Firm*—Townsend and Townsend Khourie and Crew

[57] ABSTRACT

A medication dispenser (2, 120) is used to directly fill a syringe (8, 134) with measured amounts of one or more liquid medications, typically two different types of insulin, from vials (4, 130) each having a septum at one end. The septum of each vial is pierced by a pair of hollow spikes (54, 56, 140, 142). One of the spikes is used to allow the liquid medication to be pumped out of the vial while the other spike is used to introduce air into the vial to replace the withdrawn liquid medication. Using a reciprocating piston-and-cylinder type pump, the vials are pressed a desired number of times according to how much medicine is to be driven into the syringe. The invention permits insulin users the freedom to quickly and easily select the proportions and amounts of insulin to be injected depending upon the user's current needs.

18 Claims, 13 Drawing Sheets

SYRINGE-FILLING MEDICATION DISPENSER

CROSS REFERENCE TO RELATED APPLICATIONS

This is related to U.S. patent application Ser. No. 07/667,319 filed Mar. 8, 1991 for Multiple Cartridge Syringe and U.S. patent application Ser. No. 07/668,278 filed Mar. 8, 1991 for Multipharmaceutical Syringe, both assigned to the assignee of the present invention, the disclosures of which are incorporated by reference.

BACKGROUND OF THE INVENTION

Therapeutic insulin is of three basic types: fast-acting, intermediate-acting and long-acting. Insulin users often use a combination of two types of insulin depending on the user's blood sugar level, the time of day, nourishment intake and expected activity. For example, insulin injected at the beginning of an active day may have more of the fast-acting insulin, while the insulin injection given at the end of the day before going to bed would likely have more intermediate or long-acting insulin.

One of the problems with conventional insulin syringes is that they are designed to inject only one type of insulin, not a combination. Although insulin can be obtained as a mixture of the two types, the mixtures are generally a preset combination, such as 70% intermediate-acting and 30% fast-acting. Thus, the prior art limits the insulin user to a set mixture of the two insulins or the need to make two separate injections.

SUMMARY OF THE INVENTION

The present invention is directed to a medication dispenser which can be used with one or more conventional medication vials to supply a conventional syringe with a desired amount of the one or more liquid medications. This permits the user to deliver medication, such as insulin, in desired amounts and proportions of each from a single, typically conventional, syringe.

The medication dispenser is typically used to directly fill a syringe with measured amounts of two or more liquid medications. The dispenser includes a body which has a number of cavities which are used to hold or position two or more liquid medication container, typically vials, and a syringe. The vials are of the type having a septum at one end. The septum of each vial is pierced by a pair of hollow spikes. One of the spikes is used to allow the liquid medication to flow out of the vial while the other spike is used to introduce air into the vial to replace the liquid medication drawn from the vial. Measured amounts of the liquid medication are pumped out of each vial while air simultaneously replaces the liquid pumped out of the vial. The replacement can be either passive, in which the act of pumping liquid medication through the liquid spike causes air to be pulled into the vial, or active, by which air is pumped into the vial at the same rate as liquid is pumped out of the vial.

The present invention finds particular utility for use in dispensing two different types of insulin into a syringe; this use is described with reference to the preferred embodiments. However, the invention could be used with a single medication as well. For example, human growth hormone is very expensive and requires accurate doses. With the present invention, two vials of human growth hormone could be mounted to the dispenser; when one vial is completely drained, the other vial could be used to keep from wasting the last bit of the growth hormone in the one vial. Also, the invention could be carried out using a dispenser usable with one medication container or three or more medication containers.

The liquid can be pumped using different types of pumps. One pump type is a reciprocating piston and cylinder type pump. With the reciprocating pump, the piston is reciprocated within the cylinder a desired number of times according to how much medicine is to be driven into the syringe. The dispenser is constructed to prevent the reverse flow of liquid into the vials. For example, with a reciprocating pump-type of dispenser, check valves can be used. Other types of dispensers, such as one using a peristaltic pump, can prevent reverse flow through the construction of the pump itself. The invention permits insulin users the freedom to quickly and easily select the proportions of insulin to be injected depending upon the user's current needs.

One of the primary advantages of the invention is that it is designed to be used with conventional syringes and conventional medication containing vials. Each of the disclosed embodiments of the invention permits the user to select the amount of one or more medications to be dispensed into a syringe through the syringe's needle cannula. The invention provides flexibility and ease of use with a relatively inexpensive dispenser.

With the present invention, the inside of the vial remains at essentially atmospheric pressure. The gas used to replace the liquid drawn out of the vial is typically air; however, other gases such as nitrogen could be used as well.

The needle cannula typically provides a relatively narrow constriction for the passage of the liquid medication. The present invention recognizes that this restriction exists and accommodates it through the construction of the fluid path between the pump and the needle cannula. With the peristaltic pump version, the hollow tubes which couple the peristaltic pump to the common fluid chamber adjacent the needle cannula are constructed so that they can expand or bulge to accommodate intermittently high flow rates by providing a resilient reservoir or chamber leading into the needle cannula. With the reciprocating pump embodiment, the flow path is partially defined by a resilient surface which can be deformed when under pressure thus enlarging the volume of the flow path to accommodate the sudden increase in the volume of liquid medication from the reciprocating pump.

Other features and advantages of the invention will appear from the following description in which the preferred embodiments have been set forth in detail in conjunction with the accompanying drawings.

DESCRIPTION OF THE PREFERRED EMBODIMENT

Figure 1:
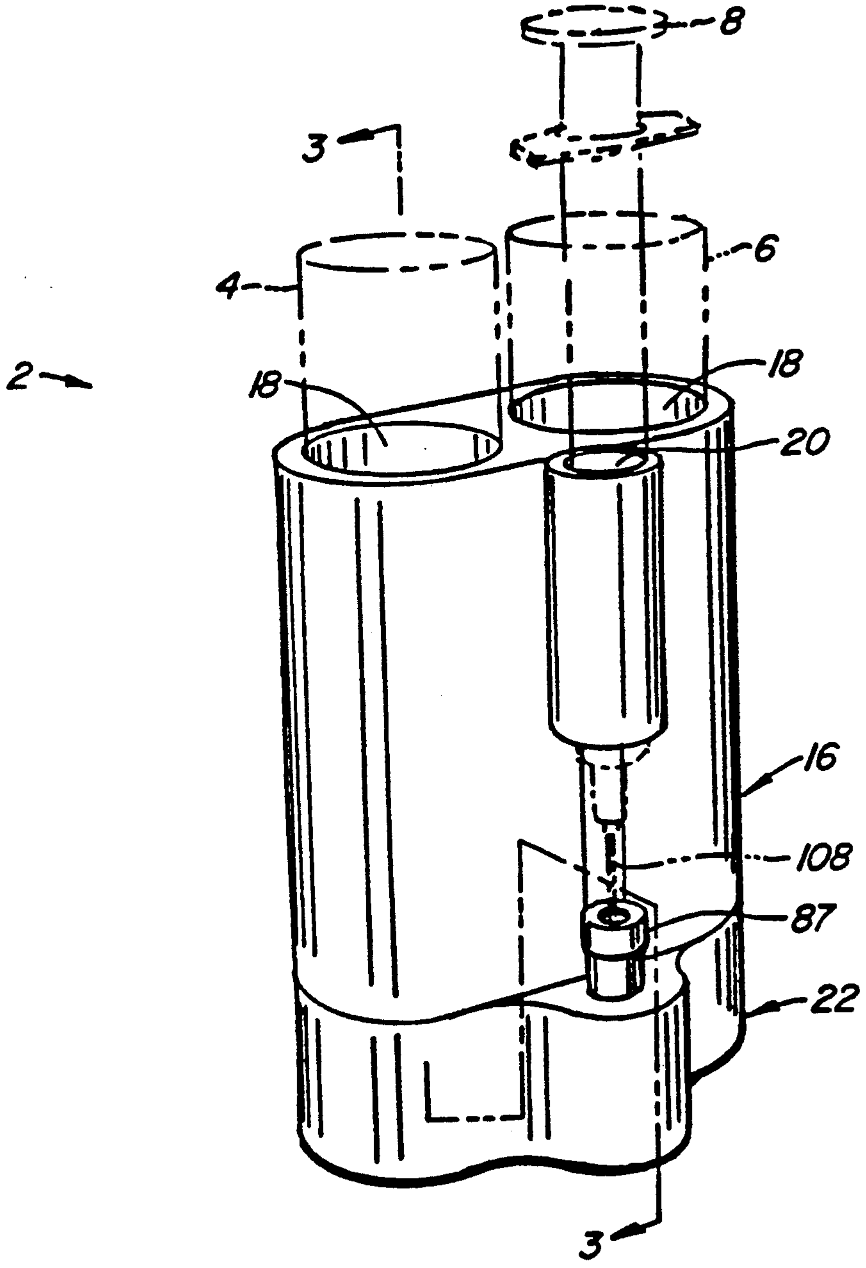
FIG. 1 is a perspective view of a reciprocating pump embodiment of a multiple medication dispenser made according to the invention with first and second vials and a syringe shown in phantom lines.
Figure 2:
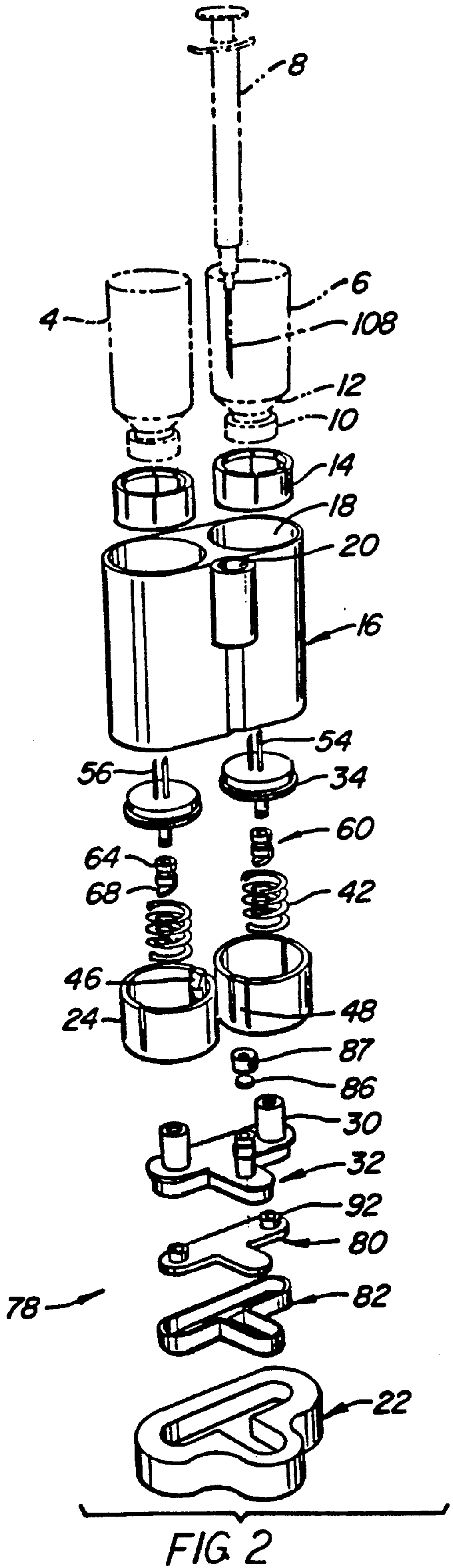
FIG. 2 is an exploded isometric view of the dispenser of FIG. 1.

FIGS. 1 and 2 illustrate a reciprocating pump type multiple medication dispenser for use with first and second vials 4, 6 and a syringe 8. The following description will discuss first vial 4 and the various components associated therewith recognizing that similar components will be present and used with second vial 6 but not described independently; this is clearly illustrated in FIG. 2. Vial 4 is of the type having a pierceable septum, not shown, held in place by a band 10 at the access end 12 of vial 4. A segmented adaptor ring 14 is mounted to vial 4 at access end 12 for the reasons described below. By the use of adaptor ring 14, different types and configurations of vials 4 can be used with only the need to change adaptor ring 14.

Dispenser 2 also includes a body 16 having vial guide bores 18 and a syringe guide bore 20. Body 16 rests on, but is freely removable from, a support base 22 as shown in FIG. 1.

Figure 3:
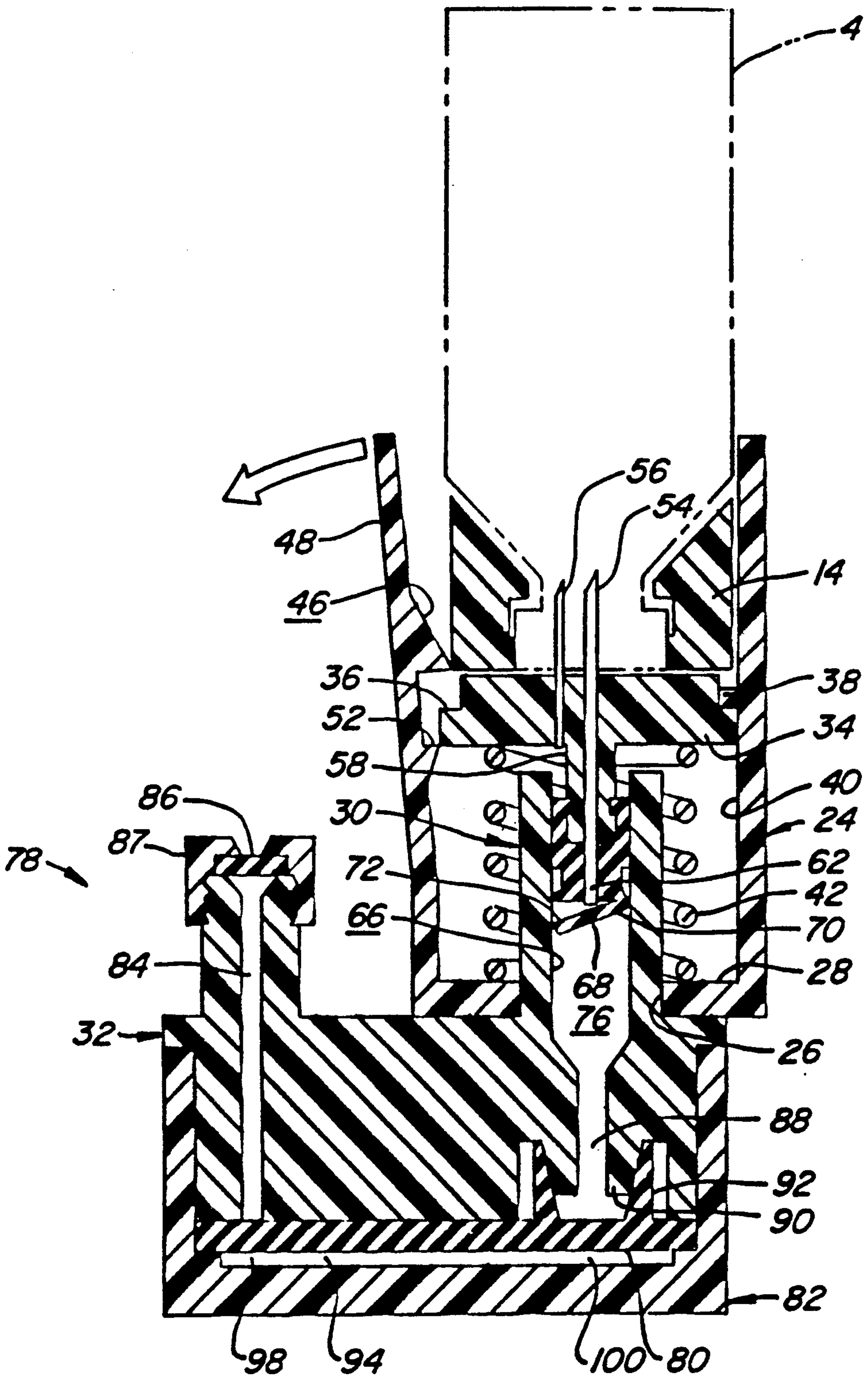
FIG. 3 is a cross sectional view taken along line 3—3 of FIG. 1 but omitting the body and the support base.

FIG. 3 illustrates the structural of FIG. 1 as viewed along line 3—3 but with body 16 and support base 22 not illustrated. Dispenser 2 includes a pair of cup-shaped split guide rings 24 each having a central opening 26 at the base 28 of guide ring 24. Opening 26 is sized to fit snugly around a cylinder 30 extending upwardly as a one piece extension from a manifold cover 32. Adaptor ring 14, body 16, split guide ring 24, cylinder 30 and manifold cover 32 are all typically made a hard plastic, such as polycarbonate. Split guide ring 24 is secured to manifold cover 32 using an adhesive, by ultrasonic welding or by other appropriate techniques.

A disk-like spike support 34 is movably mounted within each split guide ring 24. Spike support 34 has an annular ledge 36 which presses against a lug 38 extending inwardly from the inner wall 40 of split guide ring 24 by the force of a coil compression spring 42, typically made of spring-quality stainless steel. As suggested in FIGS. 4 and 5, movement of vial 4 together with adaptor ring 14 in the direction of arrow 44 causes ring 14 to engage camming surface 46 extending from the inside of resilient arm 48 in the direction of arrow 50. Doing so permits spike support 34 to disengage from an upwardly .facing ledge 52 formed on the inside of arm 48 below surface 46. This permits spike support 34 to move downwardly, in the direction of arrow 44, as discussed below.

Figure 4:
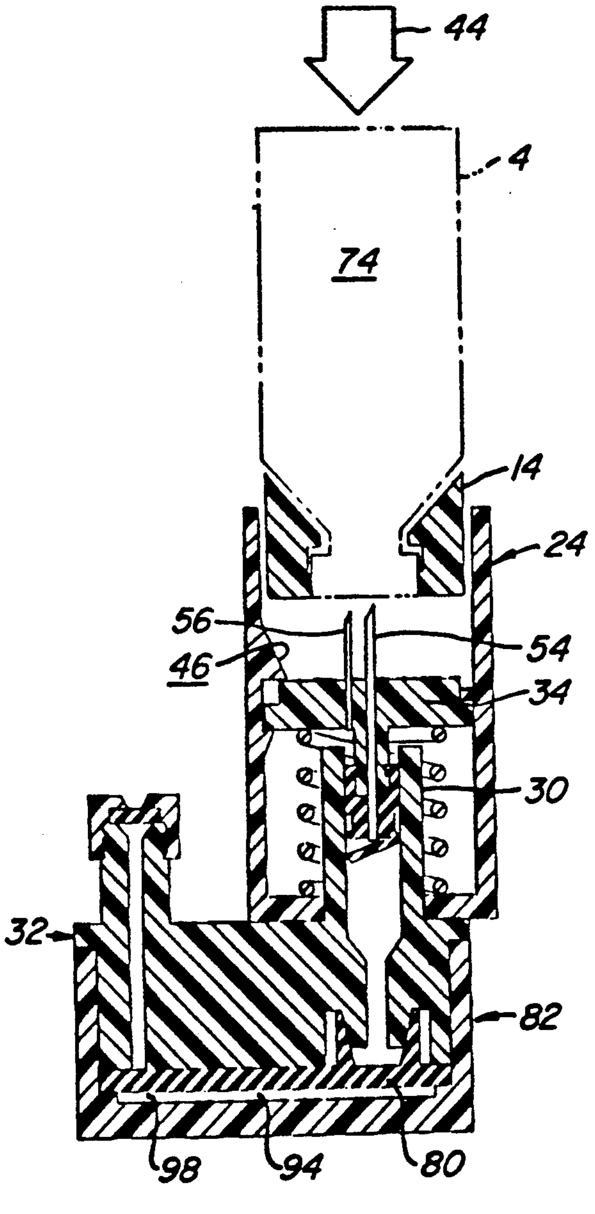
FIG. 4 shows the structure of FIG. 3 just prior to mounting a vial, to which an adaptor ring has been mounted, into the split ring guide.
Figure 5:
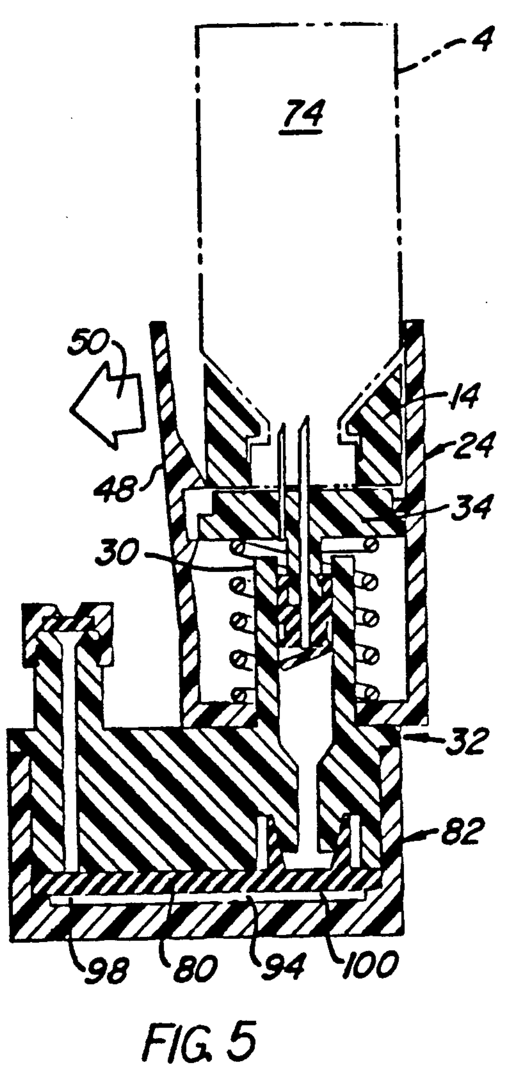
FIG. 5 illustrates the structure of FIG. 4 with the spikes fully penetrating the septum of the vial but prior to any axial movement of the piston within the cylinder.

Spike support 34 includes a pair of hollow, pointed spikes 54, 56 which are positioned to pierce the septum of vial 4 when the vial is mounted within split guide ring 24 as shown in FIGS. 4 and 5. Spikes 54 and 56 are both preferably of stainless steel. Spike 54 extends through a central bore within spike support 34 and through a cylindrical extension 58 of spike support 34. A combination piston/flapper valve 60, made of silicone rubber, is mounted to extension 58 and over the outer end 62 of liquid spike 54. Combination 60 includes a piston 64 sized to engage the cylinder wall 66 of cylinder 30. Combination 60 also includes a flapper valve element 68 which is hinged to piston 64 at position 70. The end of element 68 opposite position 70, indicated by reference numeral 72, touches cylinder wall 66 so that as piston 64 moves downwardly with respect to FIG. 3, element 68 is forced upwardly against the outer end 62 of liquid spike 54 thus sealing the liquid spike. When piston 30 moves in the opposite direction, that is upwardly with reference to FIG. 3, end 72 of element 68 also drags along wall 66 to move away from outer end 62 thus uncovering the outer end and permitting fluid communication between the interior 74 of vial 4 and interior or bore 76 of cylinder 30, which is defined by cylinder wall 66.

Figure 8:
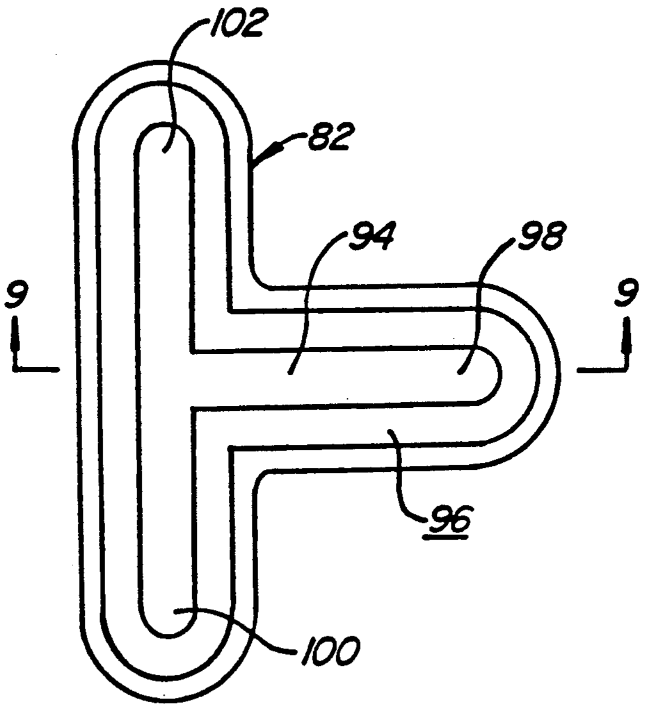
FIG. 8 is an enlarged top view of the manifold base of FIG. 2.
Figure 9:
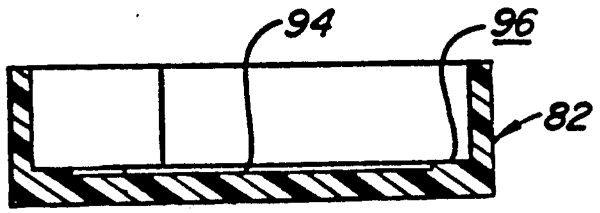
FIG. 9 is a cross-sectional view of the manifold base of FIG. 8 taken along line 9—9, the groove in the support surface of the manifold base being shown deeper than it is for purposes of illustration.
Figure 10:
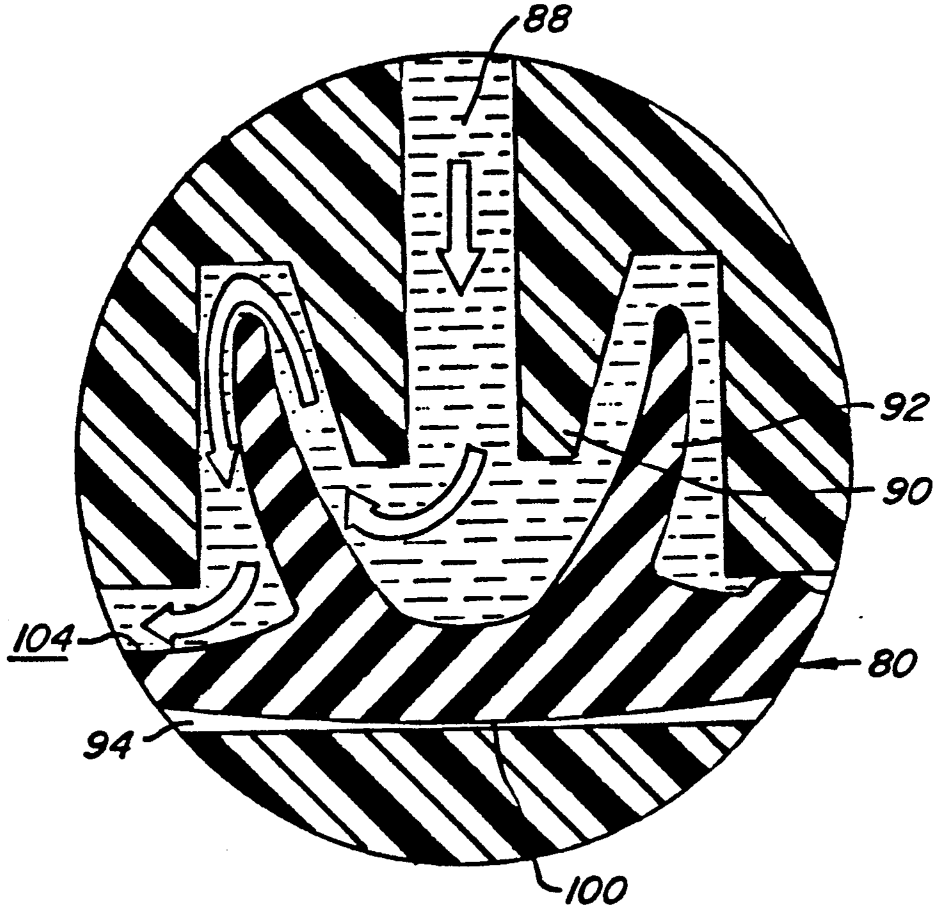
FIG. 10 illustrates in somewhat an exaggerated form the operation of the supplemental check valve formed by the tapered cup of the resilient manifold element and the externally tapered conical extension of the manifold cover.

Dispenser 2 also includes a manifold assembly 78. Manifold assembly 78 includes generally manifold cover 32, a resilient manifold element 80 and a manifold base 82. Resilient manifold element 80 is preferably made of silicone rubber while manifold base 82 is made of polycarbonate. Manifold assembly 78 defines a flow path extending from interior 76 of cylinder 30 to a needle cannula chamber 84 adjacent a needle cannula septum 86. Septum 86 is held in place by a threaded cap 87. Referring primarily to FIG. 3, interior 76 connects to a passageway 88 which passes through an externally conical element 90. Element 90 fits within an internally conically tapered cup-shaped extension 92 of resilient manifold element 80. As seen in FIGS. 8 and 9, manifold base 82 has a T-shaped groove 94 formed in its support surface 96. One end 98 of groove 94 is positioned beneath needle cannula chamber 84 while the other two ends 100, 102 are positioned below vials 4, 6. In the preferred embodiment, each arm of manifold base 82 is about 10 mm wide while groove 94 is about 0.25 mm deep and about 3 mm wide. The depth of groove 94 in the various figures has been exaggerated for purposes of illustration. The passage of the liquid medicine along the flow path will now be described with reference to FIGS. 6, 7 and 10.

Figure 6:
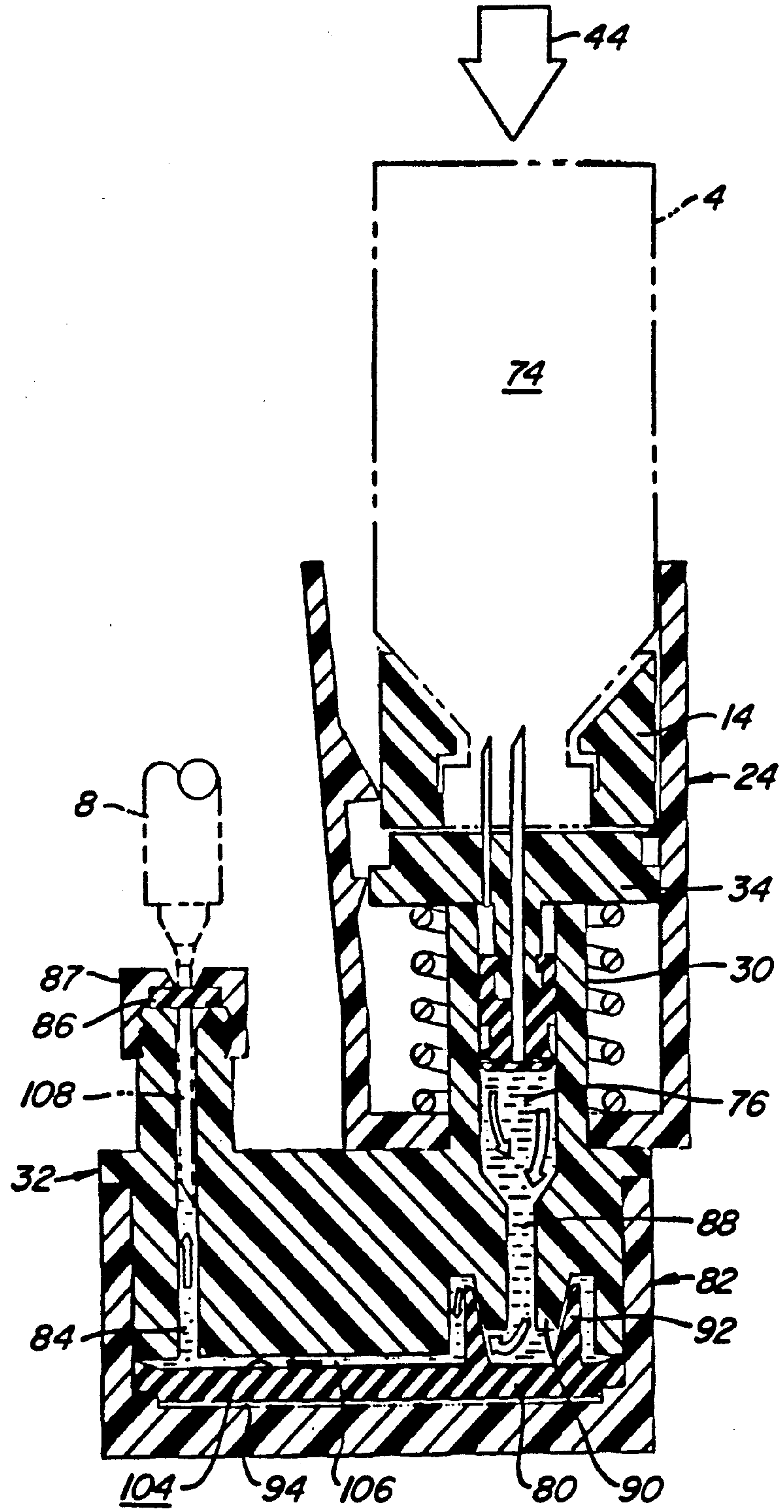
FIG. 6 illustrates the structure of FIG. 5, after the delivery stroke during which the piston moved to the delivery position, and illustrating the flow of fluid from the bore of the cylinder, along the flow path and to the needle cannula.
Figure 7:
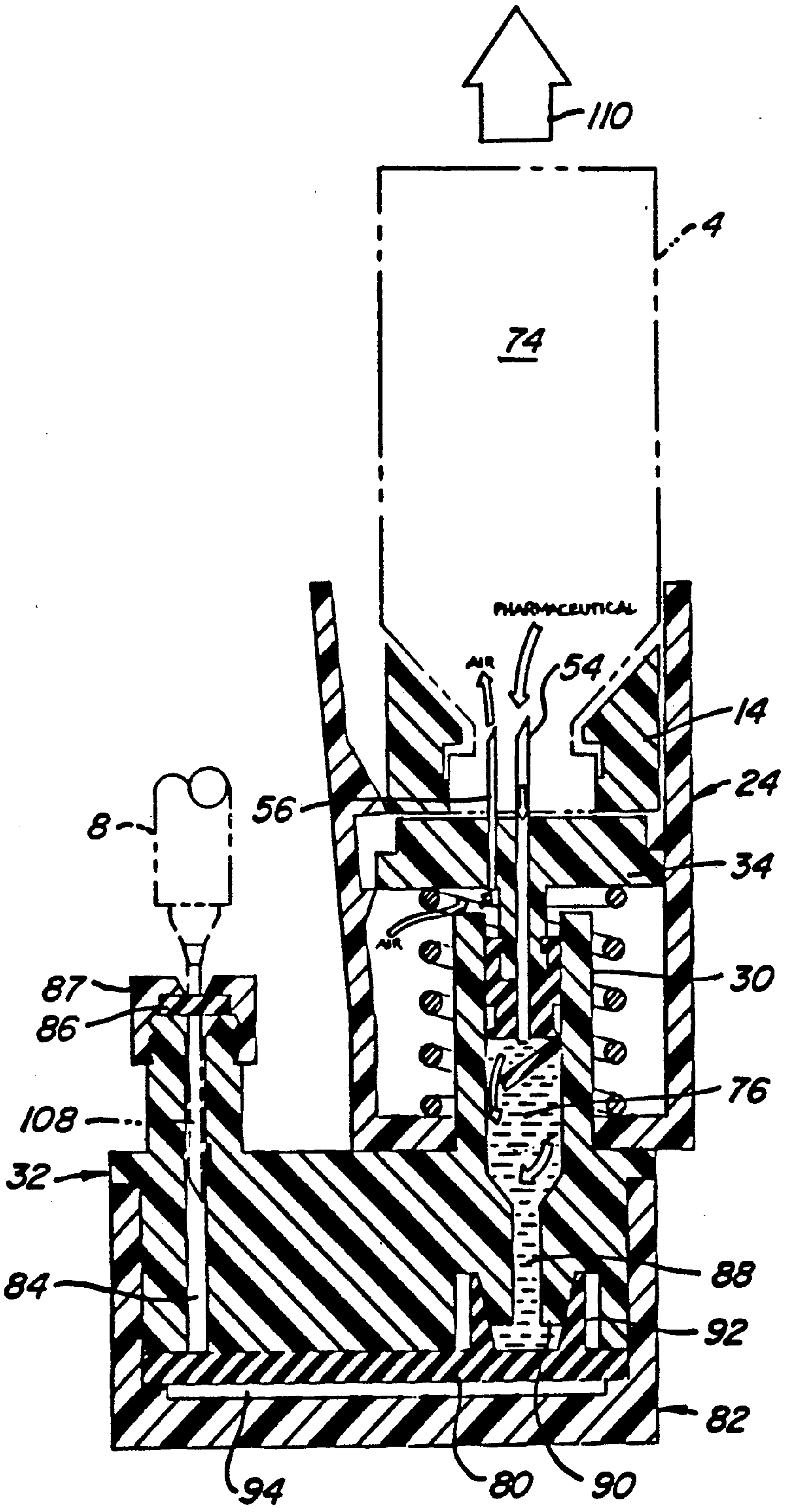
FIG. 7 illustrates the structure of FIG. 6 at the end of a replenish stroke, with the piston having moved to the replenish position, and the flow of fluid from the vial into the base of the cylinder as suggested by the arrows.

FIG. 6 shows the structure of FIG. 5 after the vial has been moved in the direction of arrow 44 from the replenish position of FIGS. 5 and 7 to the delivery position of FIG. 6 during a delivery stroke. During the delivery stroke illustrated in FIG. 6, the fluid, typically the liquid medication from within interior 74 of vial 4, is rather suddenly pressurized by the movement of piston 64. The sudden movement of liquid is resisted by the thin needle cannula 108. To accommodate the flow restriction created by having the liquid pass into syringe 8 through needle cannula 108, the flow path is configured to be resiliently expandable when subjected to pressurized fluid. This increased volume of the flow path is graphically illustrated when one compares FIGS. 6 and 7. During the delivery stroke, fluid in interior 76 is forced from interior 76 by the movement of piston 64 in the direction of arrow 44 causing the fluid to move along passageway 88. This pressurized fluid causes resilient manifold element 80 to bow downwardly, as suggested in exaggerated form in FIG. 10, into groove 94 and also causes cup-shaped extension 92 to bow outwardly permitting the fluid to move in the direction of the arrows of FIGS. 6 and 10. The fluid pressure also causes the remainder of resilient manifold element 80 to be deflected into groove 94, as can be seen by comparing FIGS. 5 and 6, so that the fluid moves along the flow path between the resilient surface 104 of element 80 and a bottom surface 106 of manifold cover 32. Thus, the region between surfaces 104, 106 along the flow path expands to accommodate the pressurization of the fluid caused by the delivery stroke.

FIG. 7 illustrates the replenish stroke during which the liquid medicine from the interior 74 of vial 4 is used to replace or replenish that which had been forced out of interior 76 of cylinder 30 during the delivery stroke. During movement of vial 4 in the direction of arrow 110, a low pressure region is formed in interior 76. This causes the supplemental valve created by conical element 90 and cup-shaped extension 92 to close. The movement of piston 64 in the direction of arrow 110 also causes end 72 of flapper valve element 68 to drag along cylinder wall 66 thus unsealing end 62 of liquid spike 54 to permit the flow of liquid medicine from interior 74, through liquid spike 54 and into interior 76 as suggested in FIG. 7. To permit this to occur, air spike 56 permits air to freely flow into interior 74 to replace the liquid pharmaceutical passing through liquid spike 54. Thus, interior 74 remains at atmospheric pressure at all times.

Figure 11:
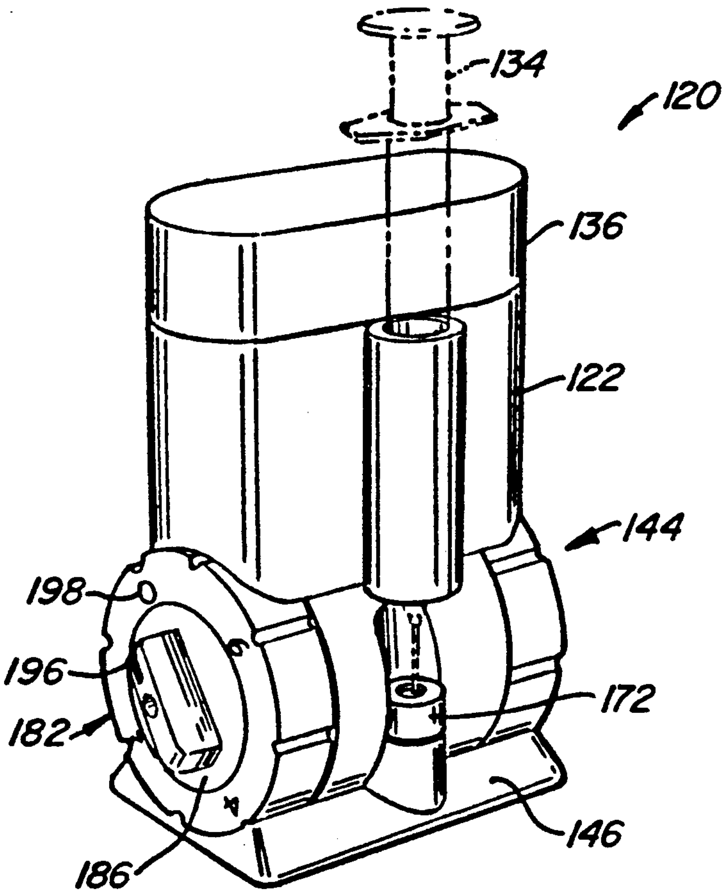
FIG. 11 is a perspective view of an alternative embodiment of the dispenser of FIG. 1 using a rotary peristaltic-type pump mechanism.
Figure 12:
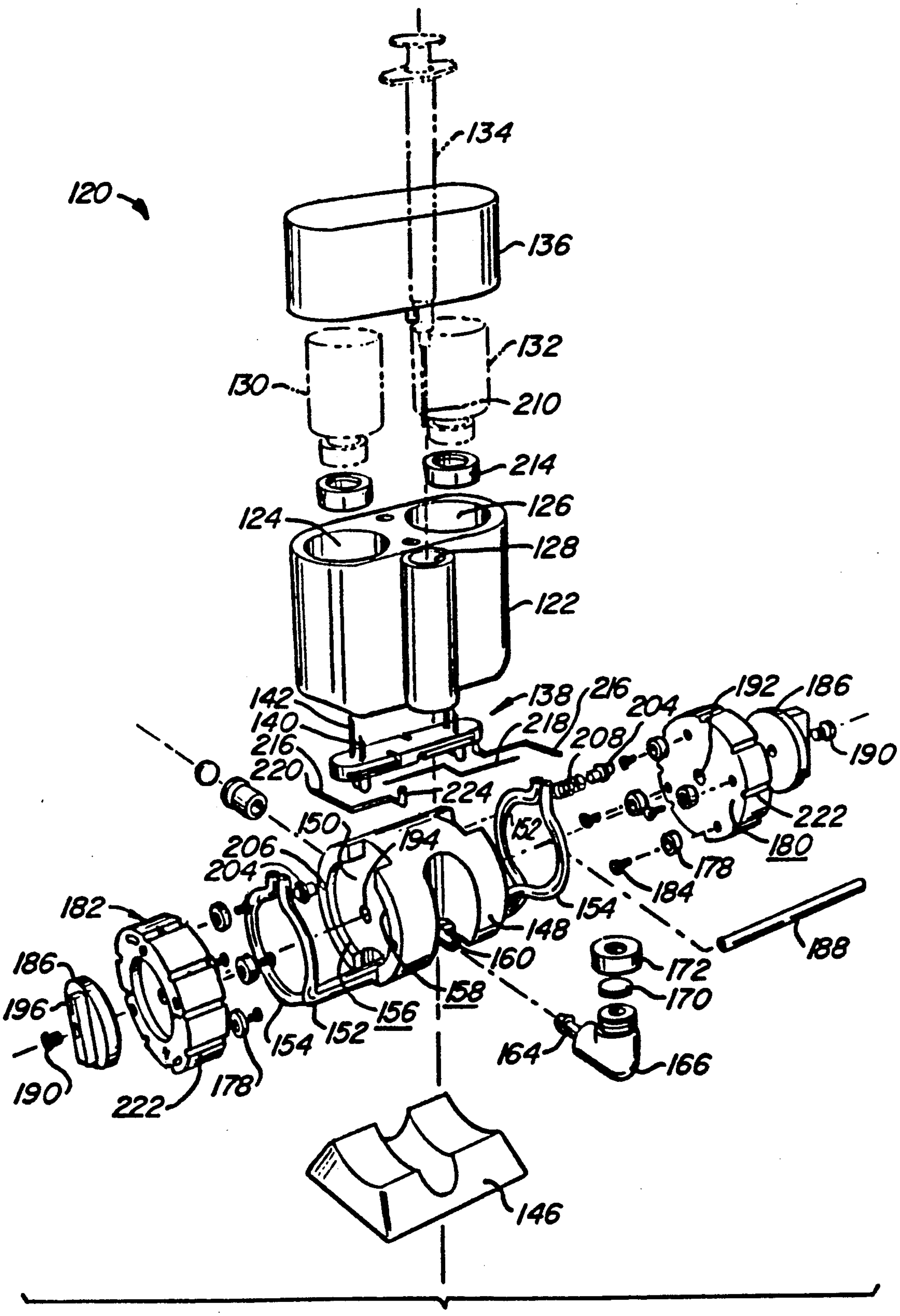
FIG. 12 is an exploded isometric view of the dispenser of FIG. 11 shown in conjunction with a pair of vials and a syringe in phantom lines.

FIGS. 11 and 12 illustrate an alternative embodiment of the invention which utilizes a peristaltic pump instead the reciprocal, piston and cylinder type of pump used with the embodiment of FIG. 1. Dispenser 120 includes a body 122 having cavities 124, 126 and 128 sized to accept vials 130, 132 and syringe 134. A lid 136 is mountable over cavities 124, 126 so to cover vials 130, 132. Dispenser 120 also includes a spike assembly 138 having two pairs of liquid and air spikes 140, 142, one pair for each of vials 130, 132. Dispenser 120 also includes a peristaltic pump assembly 144 secured to body 122 and resting on a base 146.

Figure 14:
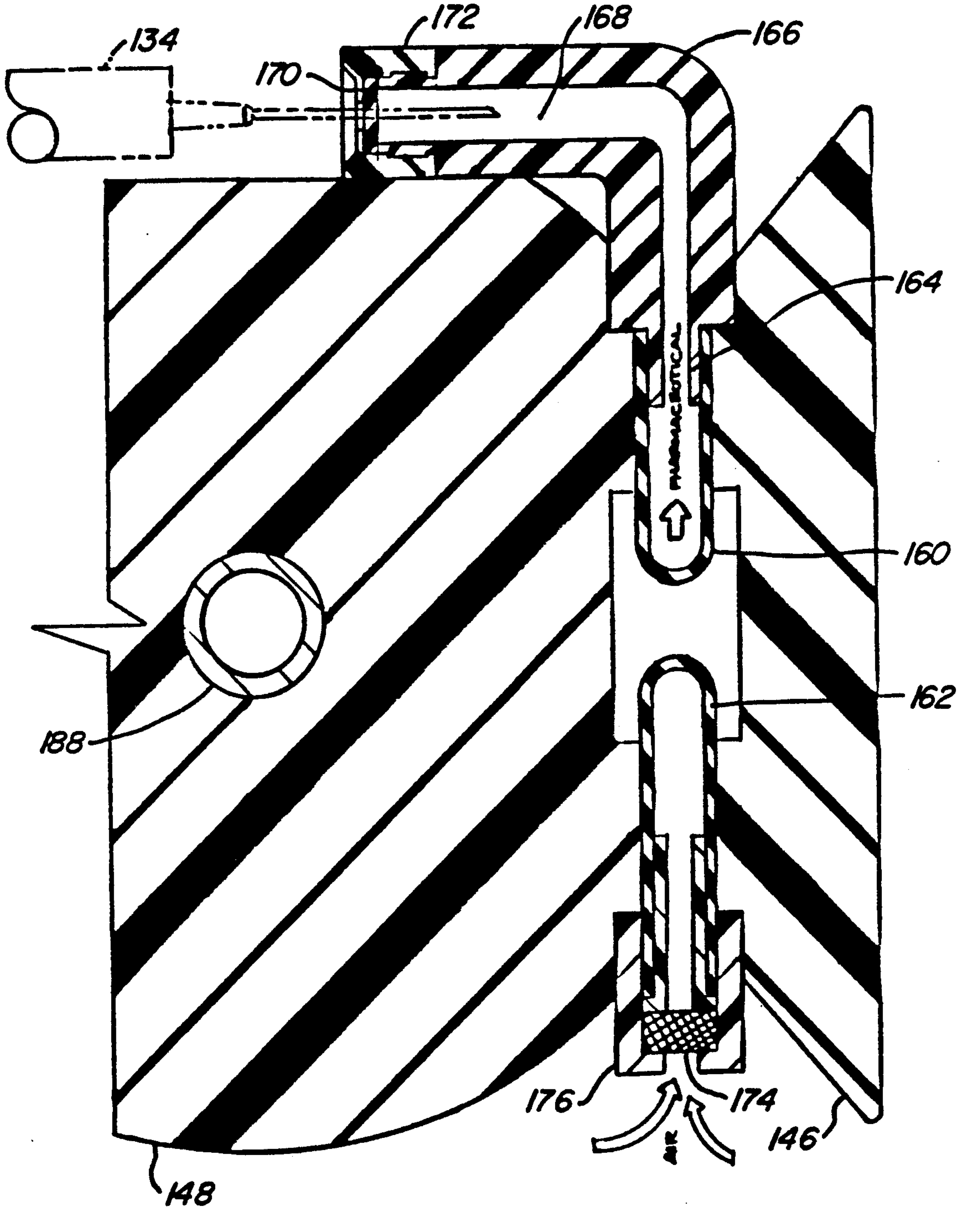
FIG. 14 is an enlarged cross sectional view of a portion of the dispenser of FIG. 11 illustrating the air intake and the septum pierceable by the needle cannula of the syringe.

Pump assembly 144 includes a pump body 148 defining a pair of generally circular recesses 150. Flexible liquid and gas tubes 152, 154 are connected to liquid and gas spikes 140, 142 at their one ends and are positioned along the accurate inner surfaces 156, 158 which bound recess 150. The other ends of tubes 152, 154 terminate at T-connections 160, 162, shown in FIG. 14. Liquid T-connection 160 connects to a fitting 164 extending from an L-shaped element 166 defining a needle cannula chamber 168 bounded by a needle septum 170. Needle septum 170 is held in place by a threaded cap 172. Air T-connection 162 has an air filter 174 mounted at its end and secured in place by an air filter cap 176.

Figure 13:
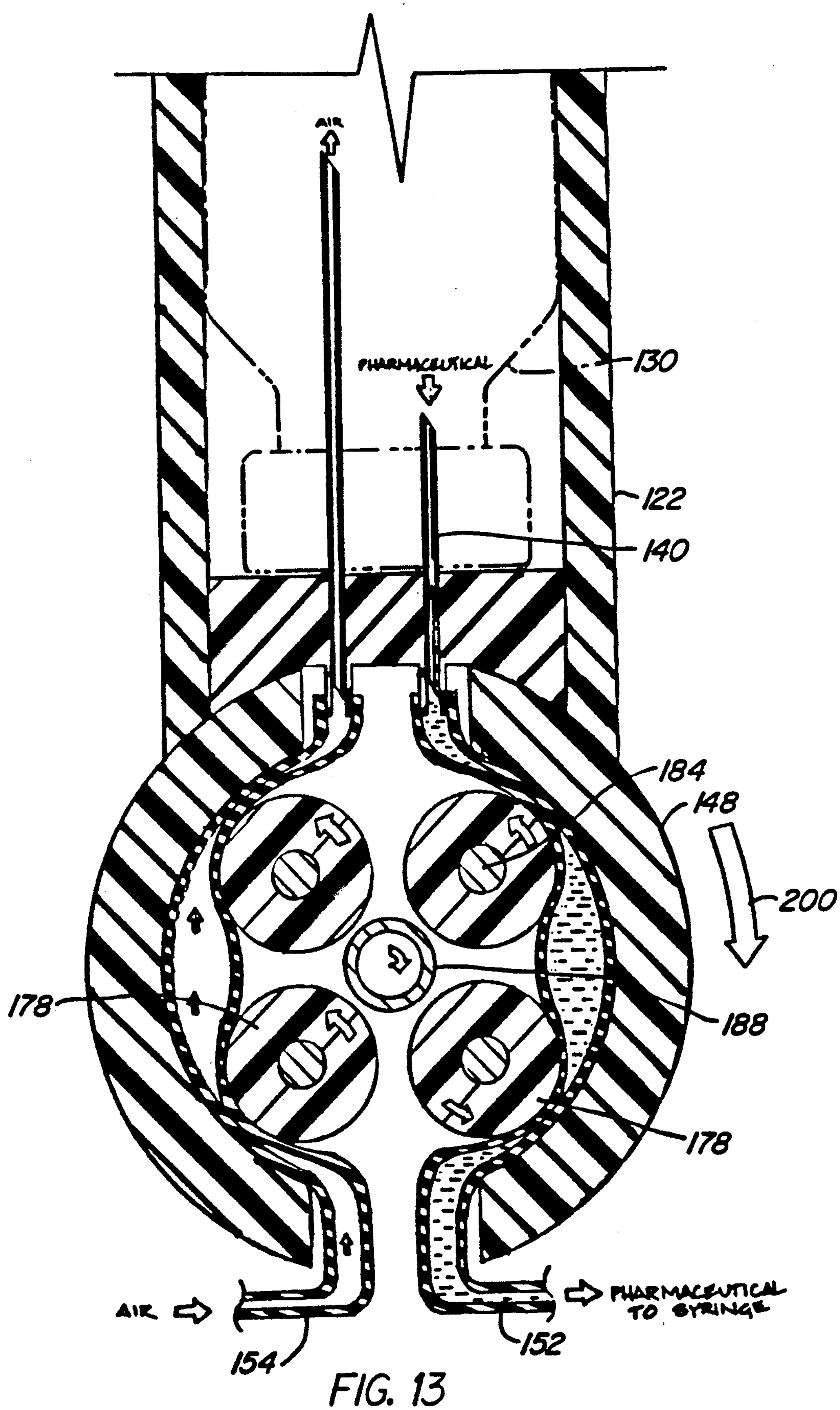
FIG. 13 is a partial cross sectional view of the dispenser of FIG. 12 showing the pumping action of the peristaltic pump.

Four peristaltic rollers 178 are rotatably mounted to the inner surface 180 of a manually rotatable dial 182 by a number of screws 184. Dials 182 are held in place by knobs 186 which are fastened to the ends of an axle 188 by screws 190; screws 190 are threaded into complementary threaded holes at the ends of the axle. Axle 188 passes through holes 192 in dials 182 and also through a center bore 194 formed in body 148. There is sufficient frictional drag among axle 188, bore 194, knobs 186 and screws 190 so that rotation of dials 182 will not cause knobs 186 to rotate as well. Knobs 186 have zero indicators 196 which are oriented with dose indicator indicia 198, typically the zero indicia, at the beginning of use. As shown in FIG. 13, rotation of dials 182 in the direction of arrow 200 will cause rollers 178 to rotate about axle 188 and also about the screws 184 securing them to dial 182. This causes air to be forced into vial 130 and liquid to be forced out of vial 130 at the same rate so that the interior of the vial remains at atmospheric pressure. Using peristaltic pumps eliminates the need for check valves.

It is preferred that dials 182 move in only one direction. To facilitate this a ratchet mechanism is used. For example, a series of ramped depressions (not shown) can be formed in surface 180. These depressions are engaged by a pin 204 having one end housed within a bore 206 formed in body 148 and the other end pressing against surface 180 in position to engage the ramped depressions. Pins 204 are biased toward surfaces 180 by a common spring 208 housed within bore 206. Other anti-reverse mechanisms can be used as well.

Figure 13A:
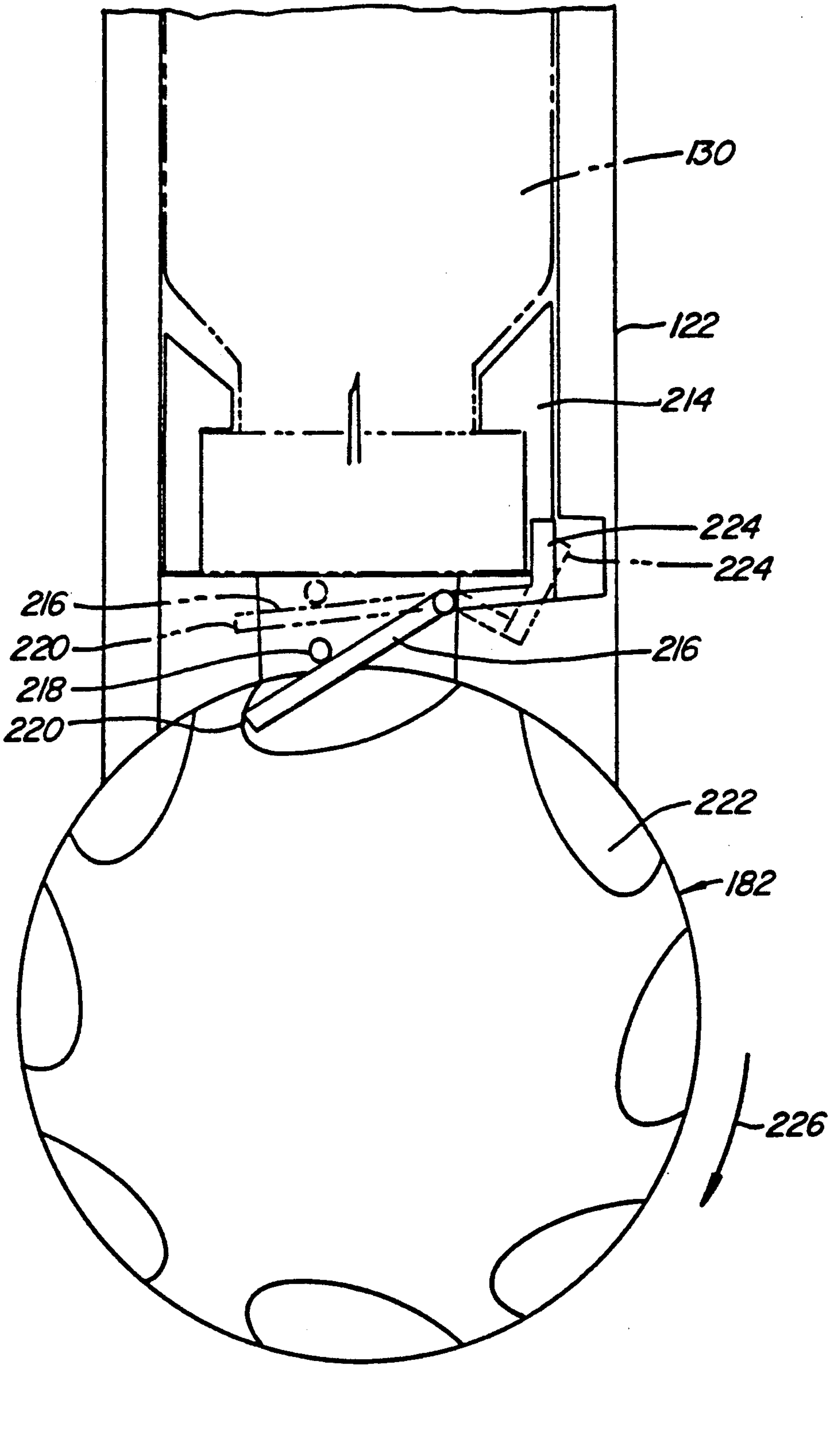
FIG. 13A is a simplified partial cross-sectional view of the dispenser of FIG. 12 showing the interlock mechanism which prevents the dials from being turned without a vial in place.

Split ring adaptors 214, see FIGS. 12 and 13A, are mounted over the ends of vials 130, 132. Ringer adaptors 214 operate to actuate interlock arms 216 when vials 130, 132 are fully within bores 124, 126 as in FIGS. 3 and 3A. Arms 216 are biased to the solid line position of FIG. 13A by a bent spring 218 so that the outer ends 220 of arms 216 engage grooves 222 formed in the outside of dials 182. When vials 130, 132 are in the positions of FIGS. 13, 13A, upstanding ends 224 of arms 216 are pushed downwardly to the dashed line position of FIG. 13A which lifts ends 220 out from groove 222 against the bias of spring 218. This prevents the rotation of dial 182 in the direction of arrow 226 unless a vial 130, 132 together with a proper adaptor ring 214 is fully mounted within body 122.

To operate dispenser 120, vials 130, 132 are placed into cavities 124, 126 so that their septums are pierced by spikes 140, 142. Lid 136 is then used to cover cavities 124, 126 and syringe 134 is mounted into syringe cavity 128 until the syringe's needle canula 210 pierces septum 170. Knobs 186 are then rotated until the respective zero indicators 196 are aligned with zero dose indicia 198. Dials 182 are then rotated an appropriate amount according to the amount and proportion of each pharmaceutical. After the appropriate amount and proportion of the pharmaceuticals are pumped into syringe 134, the syringe is removed and the injection can be given.

In both embodiments there will be an initial amount of pharmaceutical which must be pumped from the vials along the flow path before any pharmaceutical is forced into the syringe. Thus, an initiation procedure must be followed to purge the air from the flow path. One way to do this is to force one or a combination of the liquid pharmaceuticals from the vials along the flow path. Once the liquid pharmaceutical begins to enter the syringe, the syringe could be withdrawn from the dispenser, the pharmaceutical expulsed from the syringe and the syringe reinserted into the dispenser. Subsequent pump actuation would cause accurate metering of the pharmaceuticals into the syringe. Alternatively, a bleed valve could be used adjacent the needle canula septum to allow the air within the flow path to be expulsed. To ensure the proper proportion of the liquid pharmaceuticals are present in the flow path after the initialization, specialized procedures may be used. For example, if the desired mixture is equal parts of two pharmaceuticals, with the embodiment of FIG. 1 both vials 4, 6 could be pressed down, somewhat slowly, at the same time so that the fluid mixture within the flow path will be about equal parts of both liquid pharmaceuticals. In some cases the volume of liquid within the flow path is small enough not to matter insofar as proportions are concerned. Thus, any specialized procedures which may wish to be used will depend upon the particular pharmaceuticals involved, the volume of the flow path and the need to have precise proportions. For example, a small variation in the proportions between two different types of insulin may not be significant.

Other modifications and variations can be made to the disclosed embodiments without departing from the subject of the invention as defined in the following claims. For example, the invention can be carried out using one or more than two pharmaceutical vials. Also, the same medication can be used in more than one of the vials.

What is claimed is:

1. A medication dispenser, for use with a container containing a liquid medication and a syringe of the type including a needle cannula, a barrel and a plunger, the dispenser comprising:

a body to which the container and the syringe are mountable;

dual port means for providing gas and liquid ports into the interior of the container;

and a reciprocating pump assembly having a cylinder and a piston, the pump assembly fluidly coupled to the container by the liquid port and spaced apart from, and fluidly coupled to the syringe by a fluid path, the piston being movable from a first position to a second position to withdraw the liquid medication from the container, through the liquid port and into the cylinder, the withdrawn liquid medication being substantially simultaneously replaced with a gas which passes into the container through the gas port, the piston being movable from the second position back towards the first position to force a predetermined volume of the liquid medication along the fluid path and into the needle cannula of the syringe.

2. The dispenser of claim 1 wherein the body includes cavities for housing the container and the syringe.

3. The dispenser of claim 1 wherein the dual port means includes septum-piercing, hollow spikes.

4. The dispenser of claim 1 wherein the pumping means includes means for metering the amount of the liquid medication pumped into the syringe.

5. The dispenser of claim 4 wherein the metering means includes means for preventing the pumping of the liquid medication into the container.

6. The dispenser of claim 1 wherein the fluidly directing means includes a septum pierceable by the needle cannula.

7. The dispenser of claim 1 wherein the pumping means includes a piston and cylinder assembly.

8. The dispenser of claim 7 wherein the pumping means is actuated by reciprocal movement of the container.

9. The dispenser of claim 8 wherein the piston and cylinder assembly includes a cylinder and a piston, coupled to the container, for reciprocal movement with the container within the cylinder between a delivery position and a replenish position, the cylinder having a cylinder wall.

10. The dispenser of claim 9 wherein the pumping means includes a check valve fluidly coupling the container and the cylinder.

11. The dispenser of claim 10 wherein:

the check valve includes a flapper element which frictionally engages the cylinder wall as the piston moves between the delivery position and the replenish position;

the friction between the cylinder wall and the flapper element being sufficient and the flapper element constructed to cause the flapper element to seal the cylinder from the container and to fluidly couple the cylinder to the container when the piston moves towards the delivery position and towards the replenish position, respectively.

12. The dispenser of claim 1 wherein the fluidly directing means includes a supplemental check valve which permits fluid flow from the liquid port to the needle cannula but prevents fluid flow from the needle cannula to the liquid port.

13. The dispenser of claim 1 wherein the fluidly directing means includes a resilient pathway element having a flow surface which can deflect according to a fluid pressure applied thereto.

14. The dispenser of claim 13 wherein the resilient pathway element includes an elastomeric material supported on a support surface containing a groove, the elastomeric material being deflectable into the groove thereby deflecting the flow surface.

15. The dispenser of claim 1 wherein the fluidly directing means includes accumulator means for providing a pressurized liquid accumulation region to accommodate any flow restriction created by the needle cannula.

16. A multiple medication dispenser, for use with first and second containers containing first and second liquid medications and a syringe of the type including a needle cannula, a barrel and a plunger, the dispenser comprising:

a body to which the first and second containers and the syringe are mountable;

first and second dual port means for providing first and second gas and liquid ports into the interiors of the first and second containers;

first means, spaced apart from the syringe, for substantially simultaneously pumping the first liquid medication from the first container through the first liquid port and replacing the pumped first liquid medication with a first gas which passes into the first container through the first gas port;

second means, spaced apart from the syringe, for simultaneously pumping the second liquid medication from the second container through the second liquid port and replacing the pumped second liquid medication with a second gas which passes into the second container through the second gas port;

means for fluidly directing the first and second liquid medications from the first and second pumping means to the needle cannula;

whereby the first and second liquid medications are pumped from the first and second containers by the first and second pumping means, through the needle cannula and into the syringe.

17. The dispenser of claim 16 wherein:

the first pumping means comprises a first piston and cylinder assembly and is actuated by reciprocal movement of the first container;

the first piston and cylinder assembly includes a first cylinder and a first piston, coupled to the first container, for reciprocal movement with the first container within the first cylinder between a first delivery position and a first replenish position, the first cylinder having a first cylinder wall;

the first pumping means includes a first check valve fluidly coupling the first container and the first cylinder;

the first check valve includes a first flapper element which frictionally engages the first cylinder wall as the first piston moves between the delivery position and the replenish position; and the friction between the first cylinder wall and the first flapper element being sufficient and the first flapper element constructed to cause the first flapper element to seal the first cylinder from the first container and to fluidly couple the first cylinder to the first container when the first piston moves towards the first delivery position and towards the first replenish position, respectively.

18. The dispenser of claim 17 wherein the fluidly directing means includes accumulator means for providing a pressurized liquid accumulation region to accommodate any flow restriction created by the needle cannula.

* * * * *